United States Patent
Heydinger Galante et al.

(10) Patent No.: US 10,751,314 B2
(45) Date of Patent: Aug. 25, 2020

(54) COMPOSITIONS COMPRISING RUMENIC ACID-RICH CONJUGATED LINOLEIC ACID FOR JOINT HEALTH

(71) Applicant: STEPAN SPECIALTY PRODUCTS, LLC, Wilmington, DE (US)

(72) Inventors: Jenifer Heydinger Galante, Oakland, NJ (US); Hiskias Gerrit Keizer, Almere (NL)

(73) Assignee: STEPAN SPECIALTY PROFDUCTS, LLC, Wilmington, DE (US)

( * ) Notice: Subject to any disclaimer, the term of this patent is extended or adjusted under 35 U.S.C. 154(b) by 0 days.

(21) Appl. No.: 16/315,011

(22) PCT Filed: Jun. 20, 2017

(86) PCT No.: PCT/US2017/038286
§ 371 (c)(1),
(2) Date: Jan. 3, 2019

(87) PCT Pub. No.: WO2018/009334
PCT Pub. Date: Jan. 11, 2018

(65) Prior Publication Data
US 2019/0231727 A1 Aug. 1, 2019

Related U.S. Application Data

(60) Provisional application No. 62/359,718, filed on Jul. 8, 2016.

(51) Int. Cl.
*A61K 31/25* (2006.01)
*A61K 31/201* (2006.01)
(Continued)

(52) U.S. Cl.
CPC ............. *A61K 31/201* (2013.01); *A23L 33/12* (2016.08); *A61P 19/02* (2018.01); *A23V 2002/00* (2013.01)

(58) Field of Classification Search
CPC .............. A61K 2300/00; A61K 31/201; A61K 31/202; A61K 31/045; A61K 31/11;
(Continued)

(56) References Cited

U.S. PATENT DOCUMENTS

| 5,585,400 A | 12/1996 | Cook et al. |
| 5,814,663 A | 2/1998 | Cook et al. |

(Continued)

FOREIGN PATENT DOCUMENTS

| WO | 01/03688 A2 | 1/2001 |
| WO | 2005/070410 A1 | 8/2005 |

(Continued)

OTHER PUBLICATIONS

Aryaeian et al. (Int J Prev Med. Dec. 2014; 5(12): 1567-1577).*
(Continued)

*Primary Examiner* — Savitha M Rao
(74) *Attorney, Agent, or Firm* — Dilworth IP, LLC

(57) ABSTRACT

Methods for enhancing joint function and for treating or preventing age-related joint discomfort in an adult human are disclosed. The methods comprise administering to the human a dietetic food, medical food, or food supplement. The food or food supplement comprises a rumenic acid-rich conjugated linoleic acid (RAR-CLA), or a pharmaceutically acceptable salt, ester, mono-, di-, or triglyceride, metabolic precursor thereof, or mixture thereof, in an amount effective to enhance joint function or to alleviate joint discomfort in the human. The RAR-CLA comprises cis-9, trans-11 linoleic acid and trans-10, cis-12 linoleic acid isomers in a weight ratio of at least 2:1. Enrichment of a dietetic food, medical food, or food supplement with RAR-CLA can help to improve joint function and/or alleviate joint discomfort.

(Continued)

Longer-term studies should help to further elucidate the potential impact of RAR-CLA supplementation on joint function in older adults.

18 Claims, 10 Drawing Sheets

(51) Int. Cl.

| | |
|---|---|
| *A61K 31/202* | (2006.01) |
| *A23L 33/12* | (2016.01) |
| *A61K 31/045* | (2006.01) |
| *A61K 31/11* | (2006.01) |
| *A61P 19/02* | (2006.01) |

(58) Field of Classification Search
CPC ..... A61K 31/25; A23L 33/12; A23V 2002/00; A61P 25/28
See application file for complete search history.

(56) References Cited

U.S. PATENT DOCUMENTS

| | | | |
|---|---|---|---|
| 5,760,082 | A | 6/1998 | Cook et al. |
| 5,856,149 | A | 1/1999 | Pariza et al. |
| 6,184,009 | B1 | 2/2001 | Cain et al. |
| 6,395,782 | B1 | 5/2002 | Cook et al. |
| 6,838,451 | B1 | 1/2005 | Menard et al. |
| 6,897,327 | B2 | 5/2005 | Rongione et al. |
| 8,203,012 | B2 | 6/2012 | Rongione et al. |
| 8,614,074 | B2 | 12/2013 | Taran et al. |
| 2005/0154059 | A1 | 7/2005 | Cook et al. |
| 2013/0274336 | A1 | 10/2013 | Bird et al. |

FOREIGN PATENT DOCUMENTS

| | | |
|---|---|---|
| WO | 2005/107736 A1 | 11/2005 |
| WO | 2008/147228 A1 | 12/2008 |
| WO | 2016/025312 A1 | 2/2016 |

OTHER PUBLICATIONS

PCT International Search Report and Written Opinion dated Sep. 1, 2017 in corresponding Application No. PCT/US2017/038286, 15 pages.
Aryaeian et al., Int. J. Rheum. Dis. 12 (2009) 20.
Aryaeian et al., Lipids 51 (2016) 1397.
Penedo et al., J. Nutri. Biochem. 24 (2013) 2144.
Turpeinen et al., Brit. J. Nutri. 100 (2008) 112.
Sofi et al., NMCD 20 (2010) 117.
Jaudszus et al., Lipids Health Dis. 15 (2016) 21.
Yu et al., Biochim. Biophys. Acta, Mol. Cell Biol. Lipids 1581 (2002) 89.
Choi et al., Fitoterapia 86 (2013) 19.
Loeser, Osteoarthr. Cartilage 17 (2009) 971.
Collino et al., Eur. J. Pharmacol. 530 (2006) 70.
Fahmi et al., Mod. Rheumatol. 21 (2011) 1.
Kapadia et al., Front. Biosci. 13 (2008) 1813.
Matsui et al., J. Int. Med. Res. 35 (2007) 482.
Ellegaard et al., Rheumatol. Internat. 33 (2013) 65.
Greenhouse et al., Psychometrika 24 (1959) 95.
Kreider et al., J. Stength Cond. Res. 16 (2002) 325.
Jenkins et al., J. Strength Cond. Res. 28 (2014) 2127.
Aryaeian et al., Int. J. Prev. Med. 5 (2014) 1567.
Jaudszus et al., Biochimica et Biophysica Acta 1737 (2005) 111.
Nugent et al., Eur. J. Clin. Nutri. 59 (2005) 742.
Peterson et al., Antiviral Therapy 14 (2009) 33.
Viladomiu et al., Eur. J. Pharm. (2015).
Butz et al., Am. J. Physiol. Regul. Integr. Comp. Physiol. 293 (2007) R669.
Hur et al., Eur. J. Pharm. 568 (2007) 16.
Aryaeian et al., Vasc. Health Risk Manage. 4 (2008) 1423.
Huebner et al., J. Nutr. 140 (2010) 1454.
PCT International Preliminary Report on Patentability dated Jan. 17, 2019 in corresponding Application No. PCT/US2017/038286, 9 pages.

* cited by examiner

COMPOSITIONS COMPRISING RUMENIC ACID-RICH CONJUGATED LINOLEIC ACID FOR JOINT HEALTH

FIELD OF THE INVENTION

The invention relates to conjugated linoleic acid compositions and their use to maintain or enhance joint health in adult humans.

BACKGROUND OF THE INVENTION

Conjugated linoleic acids (CLA) are naturally occurring geometric and positional isomers of linoleic acid, or octadecadienoic acid, produced naturally by microbes in the rumen of ruminant animals. Numerous therapeutic uses for CLA mixtures have been reported (see, e.g., U.S. Publ. No. 2005/0154059 and U.S. Pat. Nos. 6,395,782; 5,814,663; 5,760,082; and 5,585,400).

CLA contains two double bonds separated by a single bond in a cis-, trans-configuration that commonly occurs between the 8- and 13-carbon positions. The two most common isomers of CLA are trans-10, cis-12 and cis-9, trans-11. However, while most commercial synthetic CLA supplements contain an approximately equal amount of the trans-10, cis-12 and cis-9, trans-11 isomers (i.e., a 50:50 blend), the latter represents approximately 90-95% of the total CLA in rumenic food (i.e., dairy) products. Consequently, the cis-9, trans-11 isomer is commonly referred to as rumenic acid (RA).

Methods for making RA and rumenic acid-rich conjugated linoleic acid (RAR-CLA) have been reported (see, e.g., WO 2016/025312 and U.S. Pat. Nos. 8,614,074; 8,203,012; 6,897,327; 6,184,009; and 5,856,149). For instance, WO 2016/025312 describes a method in which a CLA-based triglyceride (Clarinol G-80, product of Stepan Lipid Nutrition) is selectively hydrolyzed using a lipase catalyst to give a mixture of unconverted triglycerides and a fatty acid mixture that is enriched in rumenic acid. The fatty acid mixture is separated by wiped-film evaporation from the less-volatile triglyceride component. The triglyceride component, which is enriched in the trans-10, cis-12 isomer, is also desirable as a therapeutic agent (see, e.g., U.S. Publ. No. 2013/0274336).

Rumenic acid has shown promise as an anti-inflammatory dietary supplement in humans. For example, L. Penedo et al. (*J. Nutri. Biochem.* 24 (2013) 2144) reported that 8 weeks of RA-enriched butter improved inflammatory markers in young, healthy men and women. A. Turpeinen et al. (*Brit. J. Nutri.* 100 (2008) 112) reported that 8 weeks of RA supplementation reduced the allergic responses mediated by inflammation in young men and women with birch pollen allergy. F. Sofi et al. (*NMCD* 20 (2010) 117) showed that 10 weeks of dietary supplementation with cheese naturally rich in RA (e.g., pecorino) reduced inflammation in middle-aged men and women. Therefore, despite limited applied studies in humans, existing evidence suggests that RA may have anti-inflammatory effects.

The mechanism of action for the anti-inflammatory effects of RA may be due to its actions as an agonist of peroxisome proliferator-activated receptor-γ (PPARγ). PPARγ is a ligand-activated transcription factor that regulates gene transcription. PPARγ is expressed in most tissues of the body and has important metabolic and inflammatory effects. A. Jaudszus et al. (*Lipids Health Dis.* 15 (2016) 1) demonstrated that RA reduced inflammatory responses in human epithelial cells via activation of PPARγ. Similarly, Y. Yu et al. (*Biochim. Biophys. Acta, Mol. Cell Biol. Lipids* 1581 (2002) 89) showed that RA activated PPARγ and served as an antioxidant in mouse macrophage cells. Therefore, investigators have suggested that RA may have therapeutic value in the management of conditions characterized by chronic inflammation such as atherosclerosis, asthma, inflammatory bowel disease, obesity, and aging.

Aging is also characterized by greater oxidative stress in tissues such as cartilage (H. Choi et al., *Fitoterapia* 86 (2013) 19 and R. Loeser, *Osteoarthr. Cartilage* 17 (2009) 971). N. Aryaeian et al. (*Int. J. Rheum. Dis.* 12 (2009) 20) studied the effects of a 50:50 isomeric blend of RA and trans-10, cis-12 CLA on symptoms of rheumatoid arthritis. The authors observed a decrease in disease activity, pain, and stiffness with CLA supplementation and hypothesized that these decreases were due to reduced inflammation suggesting that RA might have protective effects against age-related joint dysfunction and/or discomfort through anti-inflammatory and antioxidant effects. For further related studies, see Y. Chen et al., *Mol. Neurobiol.* 46 (2012) 114; M. Collino et al., *Eur. J. Pharmacol.* 530 (2006) 70; H. Fahmi et al., *Mod. Rheumatol.* 21 (2011) 1; R. Kapadia et al., *Front. Biosci.* 13 (2008) 1813; R. Loeser, supra; T. Matsui et al., *J. Int. Med. Res.* 35 (2007) 482; L. Penedo et al., supra; and A. Turpeinen et al., supra.

Although many studies have examined PPARγ's cellular effects and demonstrated RA's activity as a PPARγ agonist, few studies have examined the effects of RA on applied, functional outcomes in humans, including its impact on joint health in aging adults.

SUMMARY OF THE INVENTION

The invention relates to methods for treating or preventing age-related joint discomfort in an adult human.

In one aspect, the invention relates to a method for treating an adult human having, or at risk of having, impaired joint function. The method comprises administering to the human a dietetic food, medical food, or food supplement. The food or food supplement comprises a rumenic acid-rich conjugated linoleic acid (RAR-CLA), or a pharmaceutically acceptable salt, ester, mono-, di-, or triglyceride, metabolic precursor thereof, or mixture thereof, in an amount effective to improve joint function in the human. The RAR-CLA comprises cis-9, trans-11 linoleic acid and trans-10, cis-12 linoleic acid isomers in a weight ratio of at least 2:1.

In another aspect, the method comprises treating an adult human having age-related joint discomfort. The method comprises administering to the human a dietetic food, medical food, or food supplement comprising RAR-CLA, or a pharmaceutically acceptable salt, ester, mono-, di-, or triglyceride, metabolic precursor thereof, or mixture thereof, in an amount effective to alleviate joint discomfort in the human. The RAR-CLA comprises cis-9, trans-11 linoleic acid and trans-10, cis-12 linoleic acid isomers in a weight ratio of at least 2:1.

Overall, our results show that enrichment of a dietetic food, medical food, or food supplement with RAR-CLA may help to improve joint function and alleviate age-related joint discomfort in humans.

DETAILED DESCRIPTION OF THE INVENTION

Figure 1:
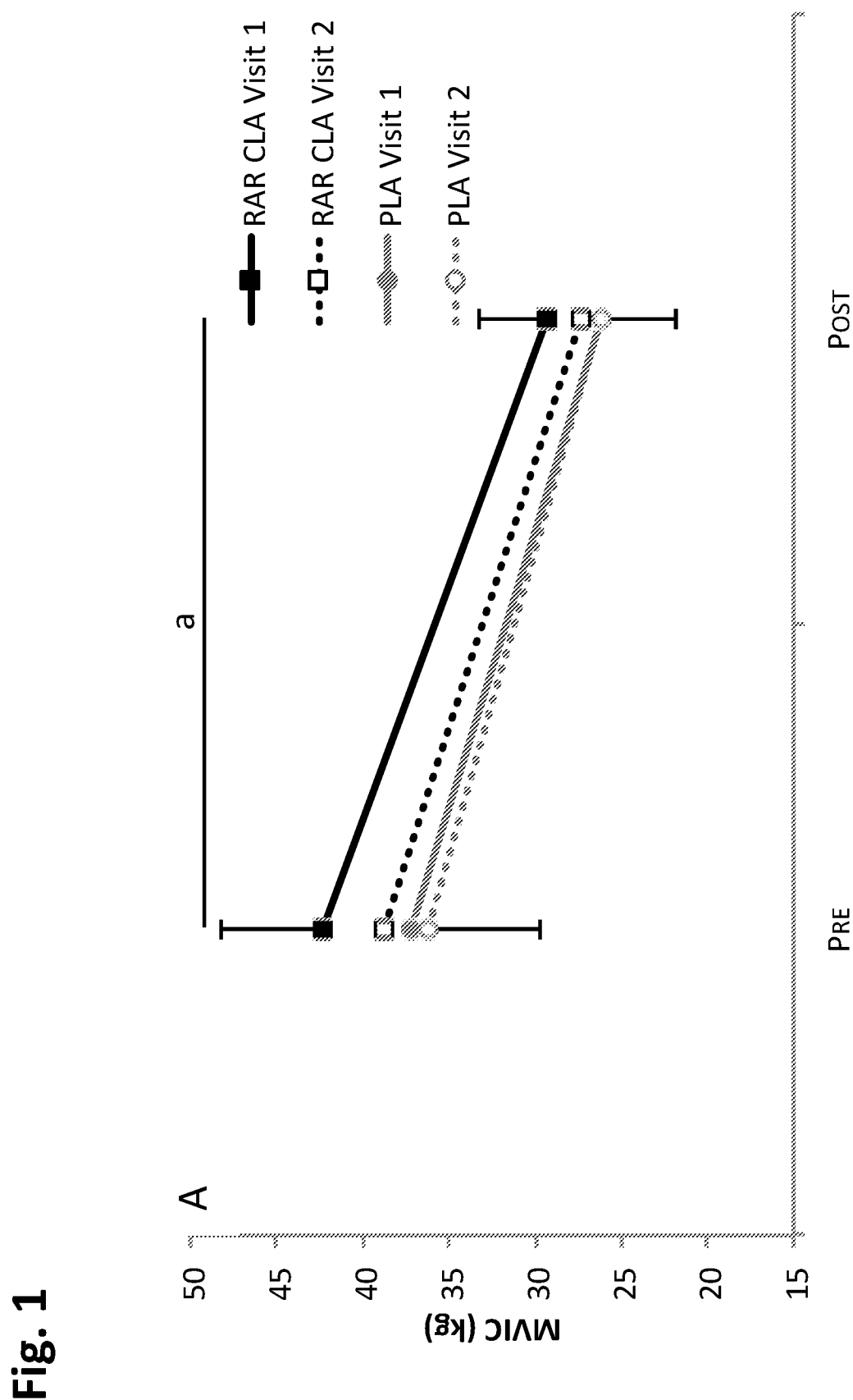
FIGS. 1 and 3 show maximal voluntary isometric handgrip contraction (MVIC) strength before (Pre) and after (Post) the handgrip fatigue test in the RAR CLA and placebo (PLA) groups at Visit 1 and Visit 2 in men (A, FIG. 1) and women (C, FIG. 3). Joint discomfort before (Pre), after (Post), and 48 h after (48 h Post) the handgrip fatigue test in the RAR CLA and PLA groups at Visit 1 and Visit 2 in (B, FIG. 2) men and (D, FIG. 4) women is shown.

Methods for treating or preventing age-related impairment of joint function in adult humans in accord with the inventive subject matter are described further below.

In one aspect, the invention relates to a method for treating an adult human having, or at risk of having, impaired joint function. The method comprises administering to the human a dietetic food, medical food, or food supplement. The food or food supplement comprises a rumenic acid-rich conjugated linoleic acid (RAR-CLA), or a pharmaceutically acceptable salt, ester, mono-, di-, or triglyceride, metabolic precursor thereof, or mixture thereof, in an amount effective to improve joint function in the human. The RAR-CLA comprises cis-9, trans-11 linoleic acid and trans-10, cis-12 linoleic acid isomers in a weight ratio of at least 2:1.

By "adult human," we mean a male or female human that is at least 18 years old. In some aspects, a relatively young adult human suffering from impairment of joint function may benefit from the dietetic foods, medical foods, or food supplements described herein. In other aspects, the adult human will be suffering from age-related impairment of joint function and may be at least 40, 50, 60, 70, or 80 years old, especially at least 70 or 80 years old. In particular aspects, the adult human will have reached at least 50%, 60%, 70%, or 80% of life expectancy based on industry-accepted actuarial measures of life expectancy.

The adult human treated according to an inventive method as described herein may have actual, quantifiable impairment of joint function or may be at risk of having or acquiring impaired joint function based on hereditary factors, environmental factors, or some combination of these.

The RAR-CLA is administered to the adult human, normally by ingestion, in the form of a dietetic food, medical food, or food supplement. A "dietetic food" is any food prepared to satisfy a specific dietary need or restriction or to meet a specific dietary goal. A "medical food" is normally used under medical supervision and is specially formulated and intended to aid in dietary management of a specific medical disorder, disease, or condition for which there are distinctive nutritional needs that are not easily met by a normal diet alone. A "food supplement" (or dietary supplement) is a product intended for ingestion that contains an ingredient intended to add further nutritional value to a diet.

Food supplements as used herein may include (in addition to the RAR-CLA) vitamins, minerals, botanicals, amino acids, other nutrients, and/or other components or additives commonly used in food supplements.

The RAR-CLA can be formulated with suitable carriers such as starch, sucrose, or lactose in tablets, pills, dragees, capsules, solutions, liquids, slurries, suspensions, or emulsions. In some aspects, a tablet, pill, or capsule comprising the RAR-CLA may be coated with an enteric coating that dissolves at a pH of about 6.0 to 7.0. A suitable coating that dissolves in the small intestine, but not in the stomach, is cellulose acetate phthalate.

The RAR-CLA can be incorporated into a variety of different natural, processed, diet, and non-diet food products, including, for example, nutritional shakes or drinks, energy bars, supplements, frozen foods, candy, snacks, meats, milk, cheese, yogurt, and other fat or oil-containing foods.

In some aspects, the dietetic food, medical food, or food supplement has a lipid content and a CLA-containing portion of the lipid (e.g., fats and/or oils) content, and at least 10 wt. %, preferably at least 35 wt. % or at least 50 wt. % of the CLA-containing portion of the lipid content of the dietetic food, medical food, or food supplement comprises the RAR-CLA, salt, ester, mono-, di- or triglyceride, metabolic precursor thereof, or mixture thereof. In other words, the CLA portion of the lipid content is enriched in RA by at least 10, 35, or 50 wt. % compared with a CLA portion that is essentially a 1:1 mixture of cis-9, trans-11 and trans-10, cis-12 CLA isomers.

By "impaired joint function," we mean a reduction in an individual's ability to move joints in the fingers, wrists, elbows, shoulders, hips, knees, ankles, toes, back, or other joints, where the reduced ability is a result of a disease, disorder, or condition; heredity; environmental stress or trauma; or aging. The degree of impairment can be relatively mild, moderate, or severe. The impairment may result from, for example, osteoarthritis, rheumatoid arthritis, repetitive stress injuries, carpal tunnel syndrome, Lyme disease, or other conditions that affect the joints. "Joint discomfort" refers to pain that may be mild, moderate, or severe and which frequently accompanies impaired joint function. In particular, joint discomfort includes discomfort due to aging itself and age-related, post-exercise discomfort.

The food or food supplement comprises a rumenic acid-rich conjugated linoleic acid, or a pharmaceutically acceptable salt, ester, mono-, di-, or triglyceride, metabolic precursor thereof, or mixture thereof.

The RAR-CLA can be manufactured by any desired method. Traditional base-catalyzed isomerization of linoleic acid provides a mixture of conjugated linoleic acids (CLA) that typically contains about a 1:1 mixture of cis-9, trans-11 and trans-10, cis-12 isomers. Triglycerides from such CLA mixtures are commercially available, and include Clarinol® G-80, a product of Stepan Lipid Nutrition. Clarinol® G-80 contains about 80% of CLA, of which about 37% is the cis-9, trans-11 isomer and about 37% is the trans-10, cis-12. Because of their high CLA content, triglycerides such as Clarinol® G-80 are good starting materials for making RAR-CLA.

Suitable methods for preparing RAR-CLA are known in the art. Some of these methods are described in WO 2016/025312 and U.S. Pat. Nos. 8,614,074; 8,203,012; 6,897,327; 6,184,009; and 5,856,149, the teachings of which are incorporated herein by reference.

Preferred methods for manufacturing RAR-CLA provide a product that is enriched in the desired cis-9, trans-11 isomer (i.e., rumenic acid) while avoiding solvents, the need for further purification steps, and production of unwanted isomers. One such approach is described in WO 2016/025312. Briefly, a triglyceride based on a 1:1 mixture of cis-9, trans-11 and trans-10, cis-12 CLA isomers is first hydrolyzed using a lipase enzyme that is selective for the cis-9, trans-11 isomer to form a CLA reaction stream comprising a free fatty acid fraction and a glyceride fraction. Suitable lipases include, e.g., a lipase from *Candida rugosa* available from Amano Enzyme as AY AMANO 400SD. The reaction is stopped by deactivating the enzyme when the ratio of cis-9, trans-11 isomer to trans-10, cis-12 isomer is at least 3:1, preferably at least 5.25:1. The reaction stream is then distilled to separate the free fatty acid stream from the less-volatile glyceride fraction. The recovered fatty acid fraction comprises a mixture of wherein the ratio of cis-9, trans-11 isomer to trans-10, cis-12 isomer is at least 3:1. The product typically contains 55 to 70 wt. % of the cis-9, trans-11 CLA isomer. For more details regarding preferred processes for making RAR-CLA, see WO 2016/025312, the teachings of which are incorporated herein by reference.

In some aspects, the starting CLA material is obtained from a source of linoleic acid, such as fish oils or vegetable oils. Safflower oil is a particularly suitable source of linoleic acid for the starting material. The source of linoleic acid is processed by process techniques known in the art to obtain the starting CLA-containing material.

In one exemplary process, the triglyceride-containing material is combined with water to form a reaction mixture, and a lipase derived from *Candida rugosa* is added to the mixture. The amount of water is about 5 to 15 wt. % based on the total weight of the reaction mixture, and the amount of lipase is about 20 to about 30 ppm of the total weight of the reaction mixture. The lipase is selective for the cis-9, trans-11 isomer and selectively hydrolyzes the CLA triglycerides. The hydrolysis is conducted at a temperature of about 40° C. to 50° C., and progress of the hydrolysis is monitored by gas chromatography (GC). The hydrolysis is allowed to continue until the weight ratio of cis-9, trans-11 isomer to trans-10, cis-12 isomer is at least 5.25:1 but not more than 8.1:1 Typical reaction times for the hydrolysis reaction are about 5 to about 8 hours.

Following the hydrolysis, vacuum is applied to remove water from the reaction mixture. When vacuum reaches about 20 mm Hg, the mixture is heated to at least 80° C. to deactivate the enzyme. Optionally, the vacuum pressure can be further reduced to about 5 mm Hg to further dry the resulting CLA product stream without deactivating the enzyme.

The resulting product CLA stream, which contains both free fatty acids and glycerides, is then distilled by molecular distillation to separate the free fatty acid fraction from the glyceride fraction. Optionally, the CLA stream can be filtered to remove solids and/or enzymes prior to the distillation operation.

If desired, distillation can be accomplished by supplying the CLA stream to a wiped-film distillation apparatus or other low residence time distillation apparatus. Such a distillation apparatus minimizes the time at which the distilled stream is subject to elevated temperatures thereby preventing or at least reducing thermal rearrangement of the CLA into undesirable isomers. For example, residence times of less than 2 minutes are advantageous for minimizing the potential for thermal rearrangement of the double bonds at elevated temperatures. Temperatures for the distillation can range from about 140° C. to about 190° C. depending on the distillation equipment used. The distillation apparatus is also preferably operated at a reduced pressure, such as, for example about 0.01 mm Hg to about 1 mm Hg. Such low pressures are advantageous since they allow the use of lower distillation temperatures, which is important due to the thermally labile nature of the CLAs.

One example of a suitable distillation apparatus is a wiped-film evaporator supplied by Pope Scientific, Inc. (Saukville, Wis.). The wiped film evaporator has heated walls and a condenser at the center of the unit. The CLA stream to be distilled flows down the heated walls. The CLA stream is distributed over the walls by means of a wiper, which forms a film on the heated walls. A condenser is in the center of the unit, minimizing the time at which the distilled stream is at elevated temperatures. The distillate stream flows down the condenser and the residue continues to flow down the walls of the distillation unit. Both the distillate and the distillation bottoms can be cooled upon exiting the unit by means of external heat exchangers. The internal condenser allows rapid condensation and recovery of the distilled material.

The distillation operation yields two entirely different, unique, and useful CLA product streams, one enriched in the cis-9, trans-11 isomer desired herein, and the other enriched in the trans-10, cis-12 isomer. The overhead distillate stream resulting from the wiped-film distillation is the free fatty acid fraction and comprises from about 55 weight % to about 70 weight % rumenic acid (cis-9, trans-11 CLA) and less than 10 weight % glycerides. The bottom distillation stream from the distillation is the glyceride fraction and comprises at least 40 weight % trans-10, cis-12 CLA isomer content and less than about 10 weight % free fatty acids. Advantageously, the process can be accomplished without a solvent, the use of which can require additional processing steps in order to remove it. The isomer composition of the resulting CLA product streams can be determined by GC, as is known in the art.

In addition to separating the free fatty acid fraction from the glyceride fraction, the distillation operation substantially removes non-conjugated trans-fatty acids and unwanted CLA isomers, such as the trans-, trans-isomers, from each of the product fractions without the need for further purification steps to remove the unwanted impurities and isomers. The resulting free fatty acid CLA product has less than about 2 wt. % of undesirable trans-, trans-isomers and less than about 1 wt. % trans-non-conjugated fatty acids. The resulting CLA glyceride product has less than about 3 wt. % of undesirable trans-, trans-isomers and less than about 1 wt. % of trans-non-conjugated fatty acids. The glyceride product also has a weight ratio of mono- and diglyceride to triglyceride of about 1:1.

The RAR-CLA can be supplied in the form of a pharmaceutically acceptable salt, ester, mono-, di-, or triglyceride, metabolic precursor thereof, or a mixture thereof. Pharmaceutically acceptable salts are well known, and lists have been published. Examples include acetates, adipates, ascorbates, benzoates, cinnamates, citrates, formats, fumarates, glutarates, hydrochlorides, isobutyrates, lactates, maleates, nitrates, oleates, palmitates, phosphates, salicylates, succinates, sulfates, tartrates, and the like. A variety of different esters of the RAR-CLA might be used, including, for example, ethyl or butyl esters. Commonly, the RAR-CLA might also be supplied as a glyceride ester, which could be a mono-, di-, or triglyceride. Triglycerides are particularly preferred. In some aspects, the RAR-CLA can be supplied in the form of a metabolite precursor, i.e., a compound that can be converted in the body to rumenic acid or other CLA isomers. Examples include cis-9, trans-11, cis-13-octadecatrienoic acid (which can be reduced to cis-9, trans-11-octadienoic acid), trans-11-octadecenoic acid (which can be oxidized to give cis-9, trans-11-octadienoic acid), and cis-9, trans-11-octadecadienol or cis-9, trans-11-octadecadienal (each of which can undergo oxidation to provide cis-9, trans-11-octadienoic acid). Mixtures of any of the above RAR-CLA forms can be used.

The RAR-CLA comprises cis-9, trans-11 linoleic acid and trans-10, cis-12 linoleic acid isomers in a weight ratio of at least 2:1. In preferred aspects, the RAR-CLA comprises cis-9, trans-11 linoleic acid and trans-10, cis-12 linoleic acid isomers in a weight ratio of at least 3:1. In more preferred aspects, the RAR-CLA comprises cis-9, trans-11 linoleic acid and trans-10, cis-12 linoleic acid isomers in a weight ratio of at least 3.5:1.

Any of a variety of screening tests might be used to detect and measure the impact of RAR-CLA on joint function, and some of the tests might be more revealing than others. In one useful test, for instance, maximal voluntary isometric handgrip contraction (MVIC) strength (or "handgrip strength") is determined with the dominant hand using a calibrated handgrip dynamometer as described below. This test is normally combined with an evaluation of "handgrip fatigue" by measuring how handgrip strength diminishes as a function of continued testing. The degree of joint discomfort experienced by tested subjects is also of interest and can be evaluated by well-known methods, including, for example, the visual analog scale used herein below.

The amount of RAR-CLA used is an amount effective to enhance joint function or to alleviate joint discomfort in the human, preferably as measured by at least one diagnostic test as described above. In general, the RAR-CLA, salt, ester, mono-, di- or triglyceride, metabolic precursor thereof, or mixture thereof is administered in an amount of at least 10 mg/kg human/day for at least 4 weeks, or in other aspects, in an amount within the range of 50 to 200 mg/kg human/day for at least 8 weeks. Longer-term studies should help to elucidate the potential impact of RAR-CLA on joint function in older adults.

The following examples merely illustrate the invention; the skilled person will recognize many variations that are within the spirit of the invention and scope of the claims.

Experimental Design

A prospective, randomized, double-blind, placebo-controlled, parallel design clinical trial was performed. There were three visits to the laboratory: Visits 0, 1, and 2. During Visit 0, the participants were familiarized with the testing procedures and received 3-day dietary food logs. Three to seven days later, the participants returned for Visit 1 and completed pre-supplementation testing, which consisted of a series of tests to measure handgrip performance and discomfort. Following testing, participants were randomly assigned to either the supplement (RAR-CLA) or placebo (PLA) group and began 8 weeks of supplementation. Forty-eight hours after Visit 1, the participants were called on the phone to provide a joint discomfort rating. At regular 2 week intervals after Visit 1, participants were called to verify supplement compliance, collect information regarding the occurrence of adverse events, and ask about changes in dietary intake or supplement and medication usage. Following 8 weeks of supplementation, the participants returned to the laboratory for Visit 2 for post-supplementation testing, which was a replication of Visit 1. Forty-eight hours after Visit 2, the participants were again called on the phone to provide a hand joint discomfort rating. The participants recorded all food and drink consumed for 2 week days and 1 weekend day between Visit 0 and Visit 1 and during the week prior to Visit 2 in the 3-day dietary food logs provided at Visit 0. The participants continued to take their supplement (RAR-CLA or PLA) until Visit 2 when they returned all unused product.

Participants

Seventy-five (53 women, 22 men) participants were enrolled, but only the data of 65 (43 women, 22 men) participants (mean±standard deviation (SD); age=72.4±5.9 yrs; height=168.8±8.5 yrs; weight=76.1±14.4 kg; BMI=26.6±4.2 kg·m$^{-2}$) were analyzed for this study. Therefore, all the participants were protocol evaluable as opposed to intent to treat. The participants in this study were between 65 and 85 years of age inclusive, had a body mass index≤35 kg·m$^{-2}$, had not participated in any other clinical trials for 30 days prior to study enrollment, consumed <500 mg·day$^{-1}$ of aspirin, and were not taking any of the following "sartans" or "glitazones": losartan (Cosaar™), candesartan (Atacand™), valsartan (Diovan™), irbesartan (Aprovel™, Karvea™, and Avapro™), telmisartan (Micardis™), eprosartan (Teveten™), olmesartan (Benicar™), azilsartan (Edarbi™, Edarbyclor™), fimasartan (Kanarb™), candesartan (Atacand™), rosiglitazone (Avandia™), and/or pioglitazone (Actos™). In addition, all participants had stopped eating≥3 servings of fish per week and taking any anti-inflammatory dietary supplements such as quercetin, curcumin, resveratrol, and/or other flavonoids for at least 1 month prior to the study. Participants were also instructed not to consume any amount of non-steroidal anti-inflammatory drugs or acetaminophen on the days of Visits 1 or 2. This study was approved by the university's Institutional Review Board for the protection of human subjects, and all subjects completed a health history questionnaire and informed consent document prior to any testing.

Supplementation

Each subject consumed six 1-g capsules per day split into two doses: a) 3 capsules of RAR-CLA or placebo at breakfast and (b) 3 capsules at dinner. Each RAR-CLA capsule contained approximately 0.58 g of rumenic acid (55-60% of total oil in each capsule). Therefore, each subject in the RAR-CLA group consumed approximately 3.5 g of rumenic acid per day. Each PLA capsule contained 1 g of high oleic sunflower oil. Therefore, each subject in the placebo group consumed approximately 6 g of high oleic sunflower oil. The manufacturing and blinding of the RAR-CLA and PLA supplements were provided to the study site by Stepan Specialty Products, LLC (Koog aan de Zaan, The Netherlands). The participants' compliance was assessed by expressing the number of RAR-CLA or PLA capsules consumed during the supplementation period as a percentage of the number of capsules that was intended to be consumed (% Compliance) as follows:

$$\frac{\text{number of capsules consumed during supplementation}}{\text{number of capsules intended to be consumed}} \times 100 = \% \text{ Compliance}$$

The mean (±SD) number of days of supplementation and supplementation compliance were 55.9±1.5 days and 101.7%±9.6%, respectively. None of the participants fell below 80% compliance.

Familiarization

For familiarization purposes, the participants completed three, 4-second handgrip MVICs at Visit 0.

Handgrip Strength

Maximal voluntary isometric handgrip contraction (MVIC) strength was determined with the dominant hand using a calibrated handgrip dynamometer (TSD121C, Biopac Systems, Santa Barbara, Calif., USA). Subjects were positioned according to the recommendations of the American Society for Hand Therapy (Fess, 1992). Subjects completed three, 4-second MVICs before (pre-exercise) and one, 4-second MVIC after (post-exercise) the handgrip fatigue test at Visits 1 and 2. Participants were instructed to squeeze "as hard and as fast possible," loud verbal encouragement was provided during each muscle action, and two minutes of rest was allowed between attempts. MVIC strength was calculated as the highest 250 millisecond average force value (kg) obtained during the plateau of each MVIC. The greatest pre-exercise MVIC force value ($MVIC_{PRE}$) and the post-exercise MVIC force value ($MVIC_{POST}$) at the pre- and post-supplementation visits were used for analysis.

Handgrip Fatigue Test

Following completion of the pre-exercise MVICs at Visits 1 and 2, the participants completed intermittent (6 seconds on, 3 seconds off) voluntary isometric handgrip contractions at 50% of each subject's MVIC (see B. Bigland-Ritchie et al., *J. Appl. Physiol.* 61 (1986) 421) until they were no longer able to achieve the target force (50±5% MVIC). The number of isometric muscle actions performed was recorded ($HG_{REP}$). Immediately following completion of the fatigue test, $MVIC_{POST}$ was determined. The percent decrease in handgrip strength was determined from the pre- and post-exercise MVICs at visits 1 and 2 using the following formula:

$$\frac{MVIC_{PRE} - MVIC_{POST}}{MVIC_{PRE}} \times 100 = \% \text{ Decrease}$$

Hand Joint Discomfort

A visual analog scale (VAS; Schlenker Enterprises Ltd., Lombard, Ill., USA) was used to assess hand joint discomfort on a scale of 0-100 mm, where 0 represents no discomfort and 100 represents maximum discomfort (see K. Ellegaard et al., *Rheumatol. Internat.* 33 (2013) 65). Joint discomfort was assessed before, after, and 48 hours after the handgrip fatigue test at Visits 1 and 2. In addition, hand joint discomfort was recorded during the handgrip fatigue test and was characterized by the joint discomfort rating recorded following each repetition. The VAS scores following the repetitions at every 10% of the total repetitions performed were used for analyses (i.e., repetition 1, 10% $HG_{REP}$, 20% $HG_{REP}$, 30% $HG_{REP}$, etc.).

Dietary Assessment

Each participant completed a 3-day dietary food log prior to Visits 1 and 2. Participants were instructed to write down all food and drink (except water) that they consumed on 2 weekdays and 1 weekend day. These were entered into an online dietary analysis software (http://www.myfitnesspal.com, MyFitnessPal LLC, San Francisco, Calif.) that provided calculations of absolute daily energy intake (kcal) as well as protein (g), carbohydrate (g), and fat (g) intakes. The average intakes for energy (kcal), carbohydrate, protein, and fat across each three-day period were used for analyses.

Statistical Analyses Nineteen separate three-way (group [RAR-CLA vs. PLA]×visit [Visit 1 vs. Visit 2]×gender [men vs. women]) mixed factorial analyses of variance (ANOVAs) were used to examine average caloric intake, average carbohydrate intake, average protein intake, average fat intake, % Decrease, and $HG_{REP}$. A four-way (group [RAR CLA vs. PLA]×time [$MVIC_{PRE}$ VS. $MVIC_{POST}$]×visit [Visit 1 vs. Visit 2]×gender [men vs. women]) mixed factorial ANOVA was used to examine handgrip MVIC strength. A four-way (group [RAR CLA vs. PLA]×time [pre- vs. post- vs. 48 h post-handgrip fatigue test]×visit [Visit 1 vs. Visit 2]×gender [men vs women]) mixed factorial ANOVA was used to analyze joint discomfort. A four-way (group [RAR CLA vs. PLA]×time [repetition 1 vs. 10% $HG_{REP}$ VS. 20% $HG_{REP}$ . . . VS. 100% $HG_{REP}$]×visit [Visit 1 vs. Visit 2]×gender [men vs. women]) mixed factorial ANOVA was also used to analyze joint discomfort during the handgrip fatigue test.

Figure 10:
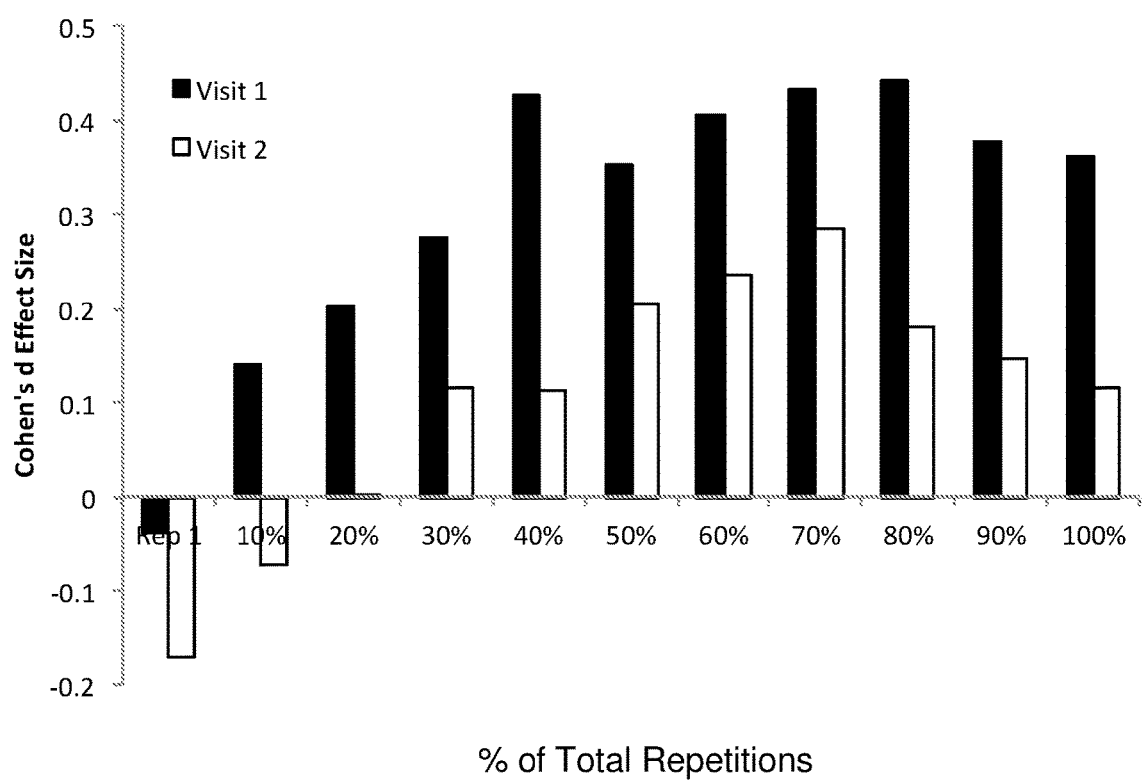
FIG. 10 shows the Cohen's d effect sizes for the differences between the RAR CLA and PLA groups (collapsed across gender) at every 10% of the total repetitions performed during the handgrip fatigue test at Visit 1 and Visit 2.

When necessary, follow-up analyses included lower order ANOVAs and Bonferonni-corrected dependent/independent samples t-tests on the simple main effects. Sphericity was tested for each repeated-measures ANOVA using Mauchly's Test of Sphericity. In cases where the assumption of sphericity was not met, Greenhouse-Geisser corrections (S. Greenhouse et al., *Psychometrika* 24 (1959) 95) were applied. Equality of variances were tested using Levene's Test for Equality of Variances for each independent samples t-test performed. In cases where the homogeneity of variances assumption was not met, the error term and degrees of freedom were adjusted using the Welch-Satterthwaite method. Partial eta effect sizes ($\eta_p^2$) were calculated for each ANOVA. Cohen's d effect sizes were calculated to examine the differences in joint discomfort between the RAR CLA and PLA groups during the handgrip fatigue test at Visits 1 and 2 (FIG. 10). The Cohen's d effect size was calculated using the formula:

$$\text{Cohen's } d = 2t/\sqrt{df}$$

where t is the independent t-test t-value and df is the degrees of freedom for the independent t-test (df=63).

Absolute change scores were calculated for each participant from Visit 1 to Visit 2 for hand joint discomfort ratings at every 10% during the handgrip fatigue test. Percent change scores were not used for joint discomfort because several participants had scores of 0 at Visit 1. Both the percent change and absolute change scores were averaged for men and women in the RAR-CLA and PLA groups and 95% confidence intervals were constructed about the means. IBM SPSS version 22 (IBM, Inc., Chicago, Ill.) and Microsoft Excel for Mac 2011 (v. 14.3.2, Microsoft Corporation, Redmond, Wash.) were used for all statistical analyses and a type I error rate of 5% was considered significant for all comparisons.

Results

Dietary Assessment

There were no significant interactions (p=0.15-0.93; $\eta_p^2$=<0.01-0.03) or main effects for group (p=0.92-0.99; $\eta_p^2$=<0.01) or time (p=0.32-0.88; $\eta_p^2$=<0.01-0.02), but there were main effects for gender (p=<0.01-0.49; $\eta_p^2$=0.06-0.14) for energy, carbohydrate, and protein fat intake (Table 1). In each instance, intake was greater in men than women. However, there were no significant interactions (p=0.30-0.89; $\eta_p^2$=<0.01-0.02) or main effects for group (p=0.84; $\eta_p^2$=<0.01), time (p=0.22; $\eta_p^2$=0.02) or gender (p=0.15; $\eta_p^2$=0.03) for fat intake.

Joint Discomfort

There were no significant interactions (p=0.29-0.90; $\eta_p^2$=<0.01-0.02) or main effects for group (p=0.21-0.53; $\eta_p^2$=0.01-0.03), visit (p=0.33-0.99; $\eta_p^2$=<0.01-0.02), or gender (p=0.62-0.86; $\eta_p^2$=<0.01) for $HG_{REP}$ and % Decrease.

There was no significant four-way interaction (p=0.97; $\eta_p^2$=<0.01) and no significant three-way (p=0.12-0.81;

$\eta_p^2$=<0.01-0.04) interactions for handgrip MVIC. There were also no two-way interactions (p=0.17-0.69; $\eta_p^2$=<0.01-0.03) or a main effect (p=0.13; $\eta_p^2$=0.04) involving group. However, there was a significant time×gender interaction (p<0.01; $\eta_p^2$=0.17). Handgrip MVIC decreased from pre- to post-handgrip fatigue test in both men and women. However, handgrip MVIC was greater in men than women at MVIC$_{PRE}$ and MVIC$_{Post}$ (Tables 3A and 3B).

For joint discomfort at pre-, post-, and 48 h post-handgrip fatigue test, there was no significant four-way (p=0.51; $\eta_p^2$=0.01) and no significant three-way (p=0.07-0.86; $\eta_p^2$=<0.01-0.05) interactions. There were also no two-way interactions (p=0.42-0.83; $\eta_p^2$=<0.01-0.01) or a main effect (p=0.90; $\eta_p^2$=<0.01) involving group. However, there was a significant time×gender (p<0.01; $\eta_p^2$=0.09) interaction. Hand joint discomfort increased from pre- to post- and then decreased from post- to 48 h post-handgrip fatigue test such that joint discomfort was lower at 48 h post-than pre-handgrip fatigue test for both men and women. In addition, joint discomfort was greater in men than women at post-, but was the same at pre- and 48 h post-handgrip fatigue test (Tables 3A and 3B).

Figure 5:
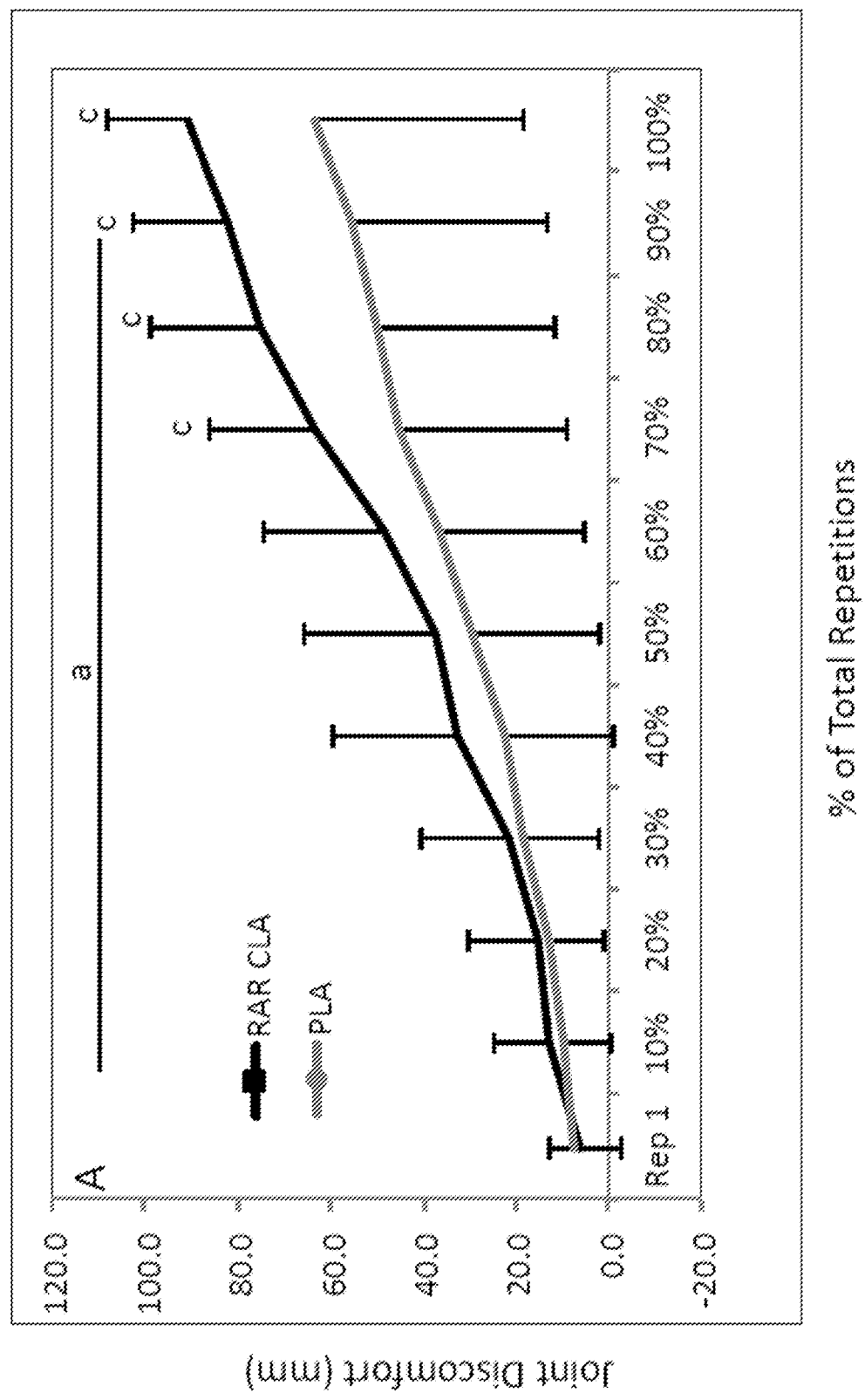
FIGS. 5-8 show joint discomfort at every 10% of the total repetitions performed during the handgrip fatigue test in the RAR CLA and PLA groups in men at Visit 1 and Visit 2 (FIGS. 5 and 7, or A and B, respectively) and women at Visit 1 and Visit 2 (FIGS. 6 and 8, or C and D, respectively).
Figure 6:
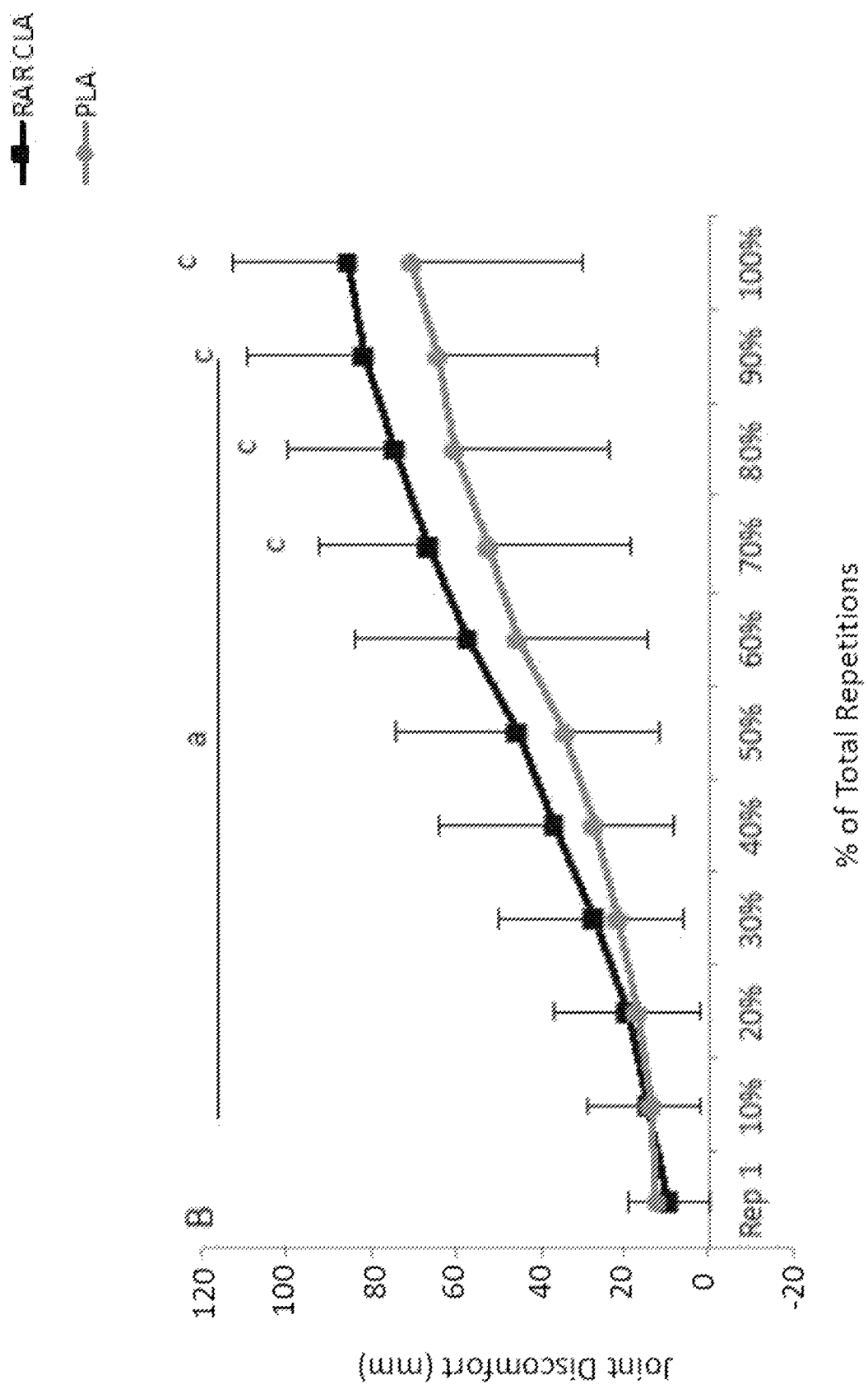
Figure 7:
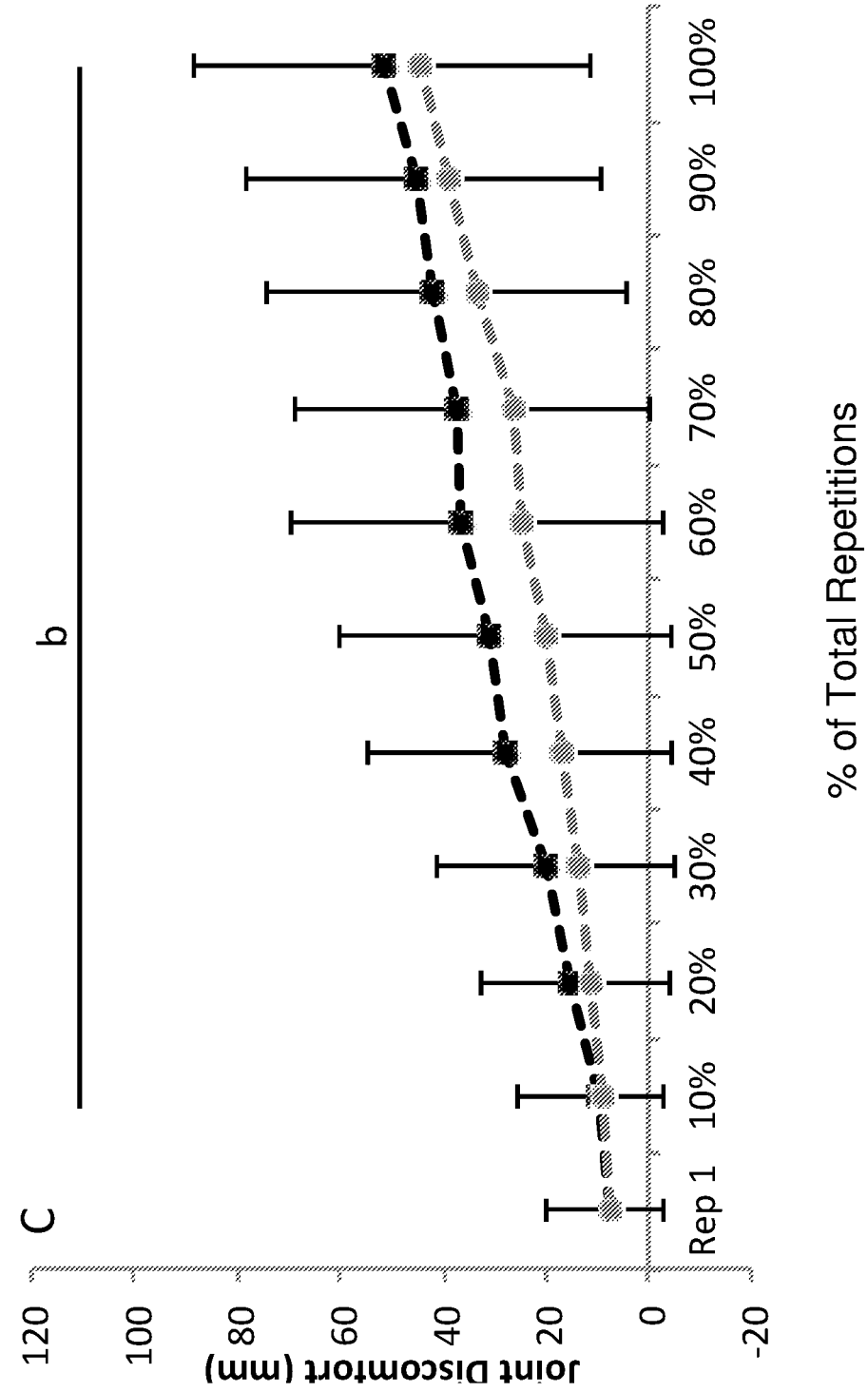
Figure 8:
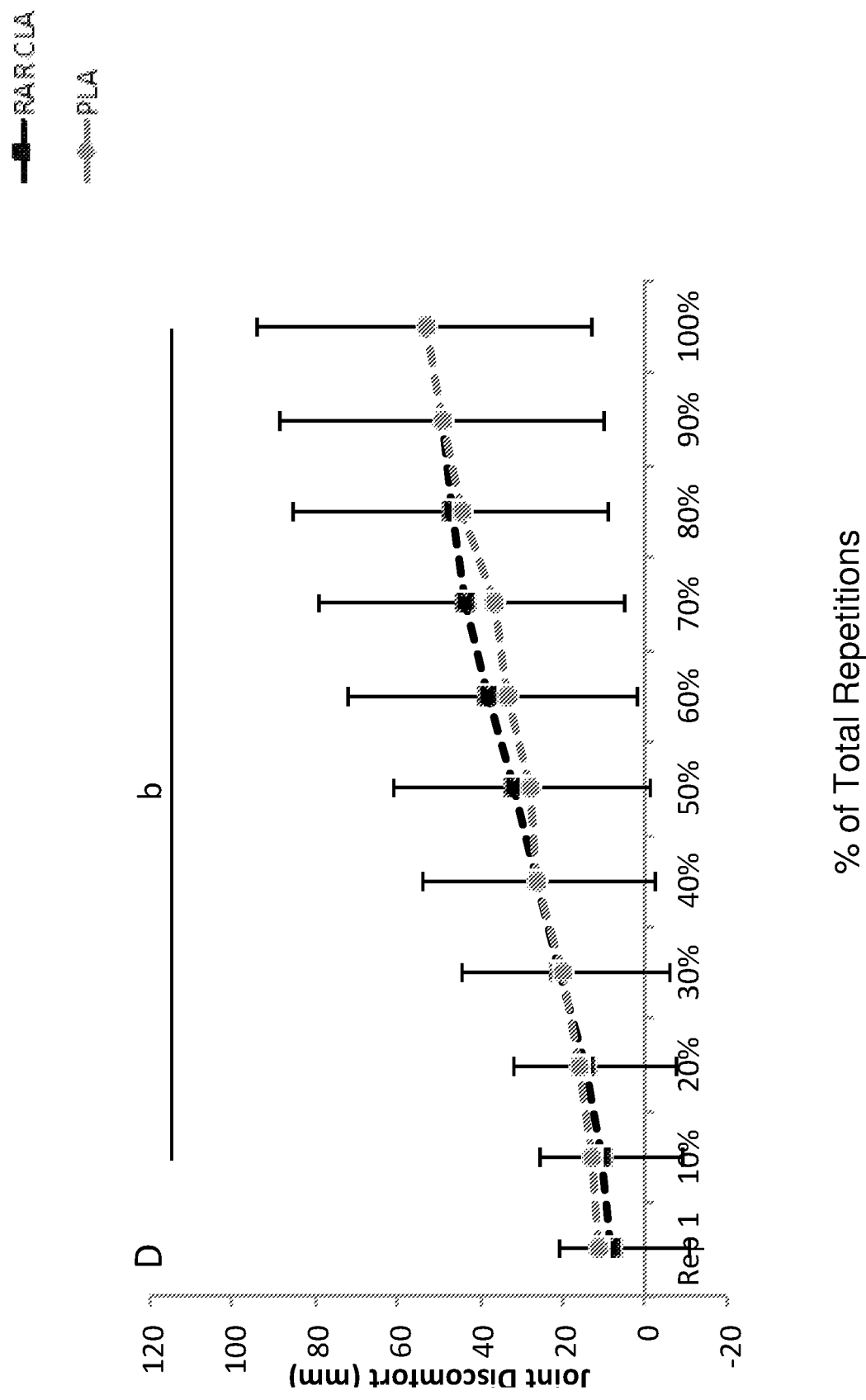
Figure 9:
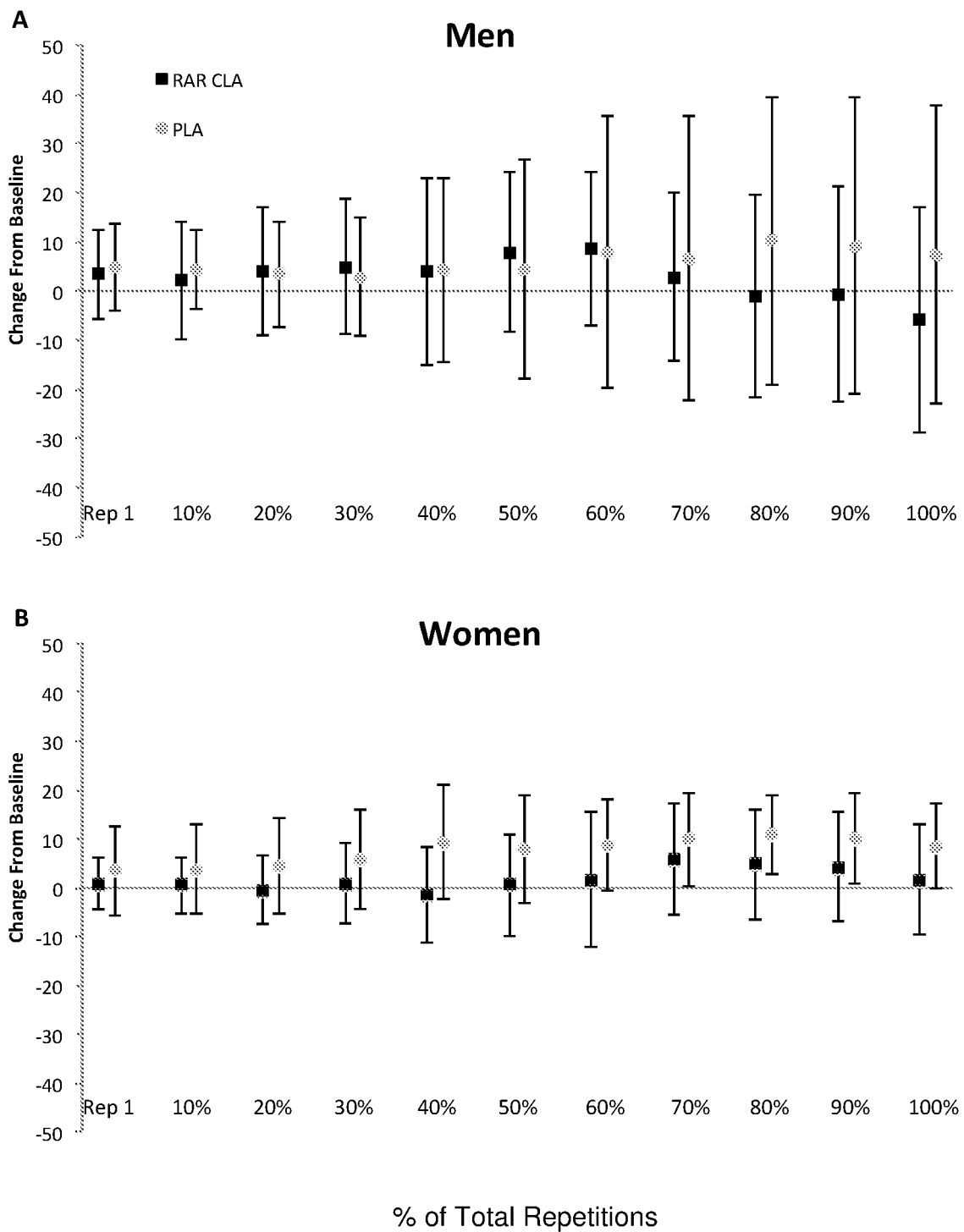
FIG. 9 shows mean (±95% confidence interval) change scores for the RAR CLA (dark squares) and PLA (grey circles) groups from Visit 1 to Visit 2 for joint discomfort ratings at every 10% of the total repetitions performed during the handgrip fatigue test in (A) men and (B) women.

For joint discomfort during the handgrip fatigue test, there was no significant four-way (p=0.78; $\eta_p^2$=0.01) and no significant three-way (p=0.32-0.65; $\eta_p^2$=<0.01-0.02) interactions. There were also no two-way interactions (p=0.09-0.56; $\eta_p^2$=0.01-0.04) or a main effect (p=0.19; $\eta_p^2$=0.03) involving group. However, there was a time×gender interaction (p<0.01; $\eta_p^2$=0.14). In men, joint discomfort increased in a cubic fashion such that joint discomfort stayed the same from repetition 1 to 20% HG$_{REP}$, increased from 20% HG$_{REP}$ to 90% HG$_{REP}$, and plateaued from 90% to 100% HG$_{REP}$ (FIGS. 5 and 7). In women, joint discomfort stayed the same from repetition 1 to 10% HG$_{REP}$ but increased linearly from 10% to 100% HG$_{REP}$ (FIGS. 6 and 8). Hand joint discomfort was also significantly greater (p<0.01) in men than women from 70% to 100% of HG$_{REP}$ (FIGS. 5-8). FIG. 9 contains the mean (±95% confidence intervals) change scores for the joint discomfort ratings in men and women in the RAR CLA and PLA groups.

Figure 2:
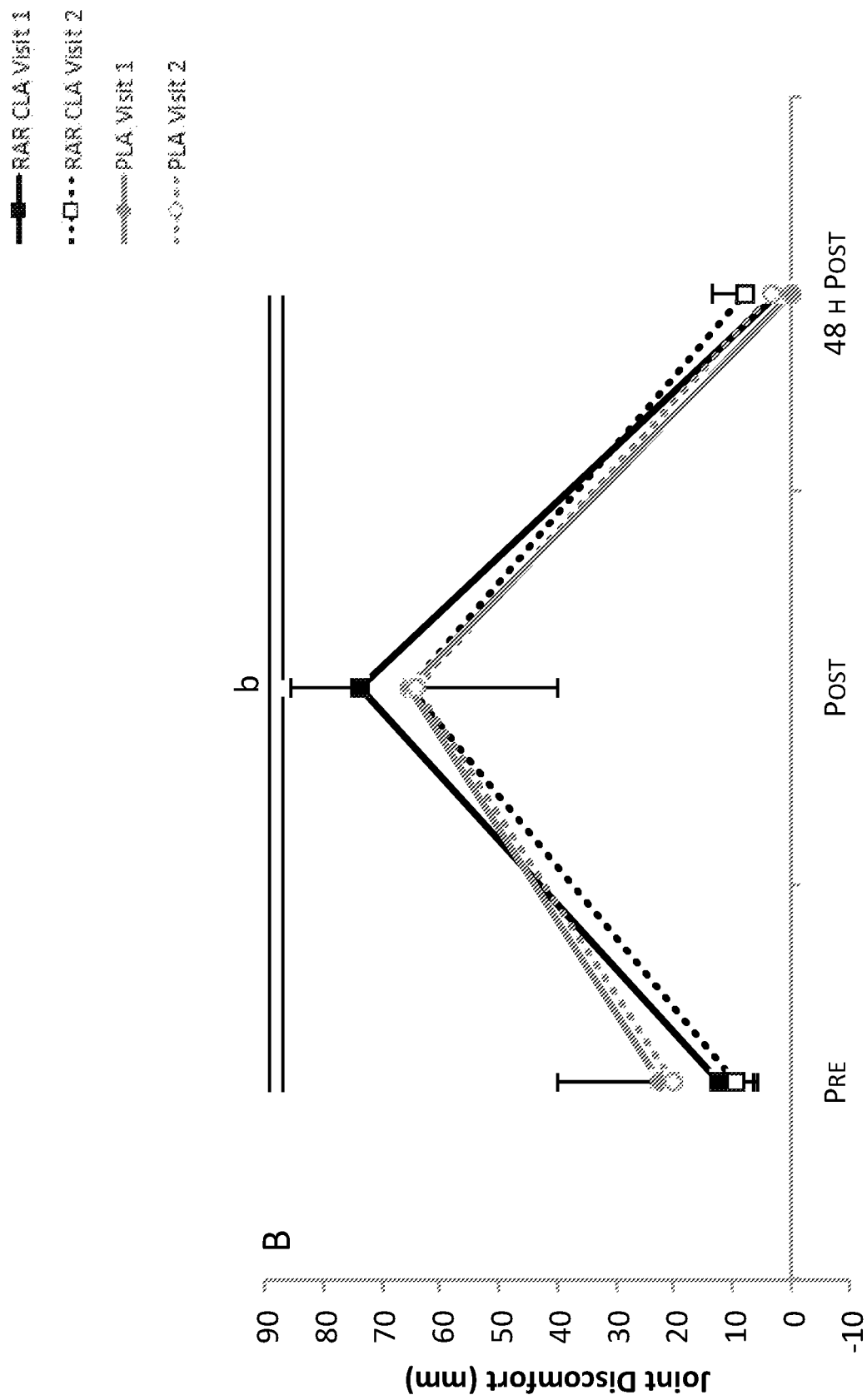
Figure 3:
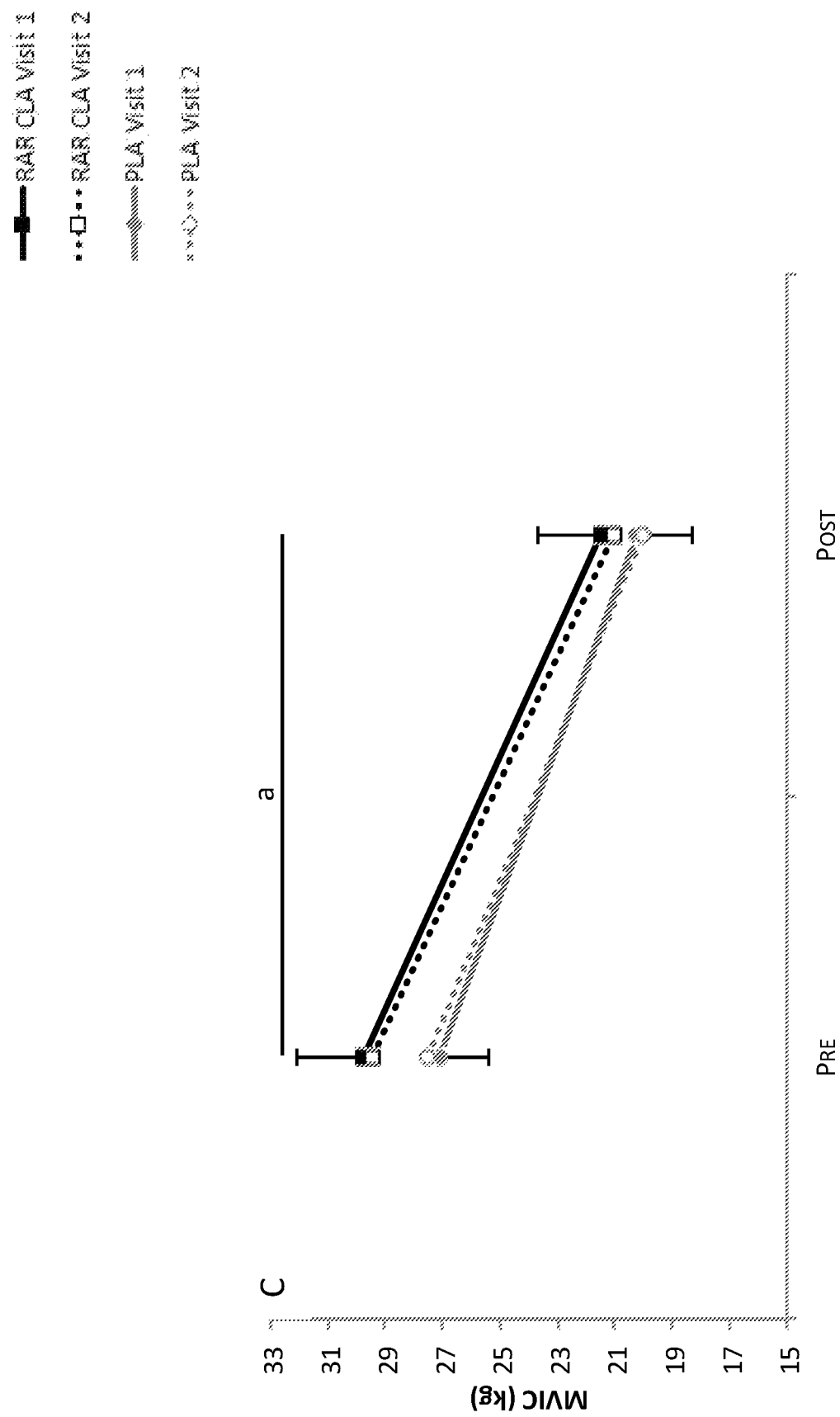
Figure 4:
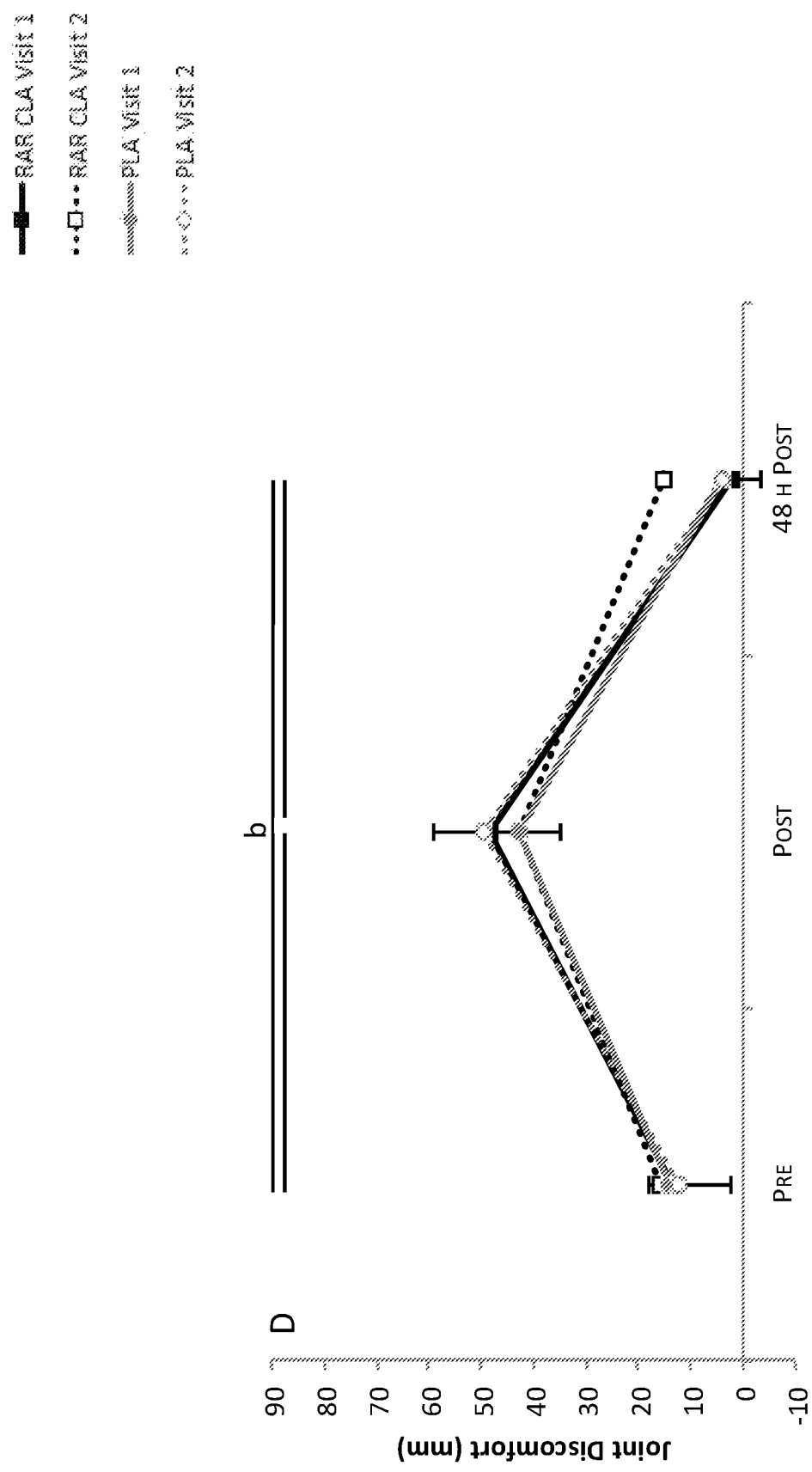

FIGS. 1 and 3 show maximal voluntary isometric handgrip contraction (MVIC) strength before (Pre) and after (Post) the handgrip fatigue test in the RAR CLA and PLA groups at Visit 1 and Visit 2 in men (A, FIG. 1) and women (C, FIG. 3). Joint discomfort before (Pre), after (Post), and 48 h after (48 h Post) the handgrip fatigue test in the RAR CLA and PLA groups at Visit 1 and Visit 2 in (B, FIG. 2) men and (D, FIG. 4) women is shown. In FIGS. 1 and 3, "a" indicates a significant time×gender interaction. Handgrip MVIC decreased from Pre to Post in men and women. Handgrip MVIC was greater in men than women at Pre and Post. In FIGS. 2 and 4, "b" indicates a significant time× gender interaction. Joint discomfort increased from Pre to Post before decreasing from Post to 48 h Post in men and women. Joint discomfort was greater in men than in women at Post.

FIGS. 5-8 show joint discomfort at every 10% of the total repetitions performed during the handgrip fatigue test in the RAR CLA and PLA groups in men at Visit 1 and Visit 2 (FIGS. 5 and 7, or A and B, respectively) and women at Visit 1 and Visit 2 (FIGS. 6 and 8, or C and D, respectively). There was a time×gender interaction for joint discomfort during the handgrip fatigue test. In FIGS. 5, and 7, "a" indicates that in men, joint discomfort increased in a cubic fashion such that joint discomfort stayed the same from repetition 1 to the 20% HG$_{REP}$, increased from 20% HG$_{REP}$ to 90% HG$_{REP}$, and plateaued from 90% to 100% HG$_{REP}$. In FIGS. 6 and 8, "b" indicates that in women, joint discomfort stayed the same from repetition 1 to 10% HG$_{REP}$ but increased linearly from 10% to 100% HG$_{REP}$. In FIGS. 5 and 7, "c" indicates that there were also significant differences in joint discomfort between men and women from 70% to 100% of HG$_{REP}$.

FIG. 9 shows mean (±95% confidence interval) change scores for the RAR CLA (dark squares) and PLA (grey circles) groups from Visit 1 to Visit 2 for joint discomfort ratings at every 10% of the total repetitions performed during the handgrip fatigue test in (A) men and (B) women.

FIG. 10 shows the Cohen's d effect sizes for the differences between the RAR CLA and PLA groups (collapsed across gender) at every 10% of the total repetitions performed during the handgrip fatigue test at Visit 1 and Visit 2. A negative effect size indicates that joint discomfort was lower in the RAR CLA group, whereas a positive effect size indicates that joint discomfort was lower in the PLA group. Therefore, a decrease in effect size from Visit 1 to Visit 2 indicates a positive effect of RAR CLA.

Discussion

The results demonstrated no treatment differences for handgrip strength or handgrip fatigue. Despite no treatment differences in the absolute hand joint discomfort values, the mean change scores indicated that, for men, hand joint discomfort tended to decrease from Visit 1 to Visit 2 at the end of the fatigue test in the RAR CLA group, but increase in the PLA group (FIG. 9, A). In women, the mean change scores for joint discomfort increased at the end of the fatigue test from Visit 1 to Visit 2 for the PLA group, but not the RAR CLA group (FIG. 9, B). Together, these data suggest that RAR CLA supplementation improves hand joint discomfort somewhat for both men and women (FIGS. 5-8 and 9).

Handgrip strength decreased from before to after the handgrip fatigue test as expected. However, there were no treatment-related changes in handgrip strength or fatigue (i.e., MVIC, % Decrease, or HG$_{REP}$). These results expand on the findings of others (see R. Kreider et al., *J. Stength Cond. Res.* 16 (2002) 325 and N. Jenkins et al. (*J. Strength Cond. Res.* 28 (2014) 2127) who demonstrated that, in younger adults, CLA had no effects on muscle strength and local muscular endurance, respectively.

There were no significant treatment differences in the absolute mean hand joint discomfort scores (Tables 3A and 3B; FIGS. 5-8). However, examining the mean change (±95% confidence interval) scores indicated that, in men, hand joint discomfort tended to decrease from 80-100% HG$_{REP}$ (FIG. 9, A) in the RAR CLA compared to the PLA group. In women, the change in joint discomfort increased from Visit 1 to Visit 2 in the PLA group at 70-90% HG$_{REP}$, but did not change in the RAR CLA group (FIG. 9, B). Therefore, from a qualitative perspective, RAR CLA supplementation may have had a positive influence on hand joint discomfort. It was shown previously (N. Aryaeian et al., supra) that 3 months of CLA and CLA+Vitamin E supplementation was beneficial for improving disease activity scores, pain, and morning stiffness in rheumatoid arthritis patients. Supplementation periods longer than 8 weeks may help to more conclusively demonstrate the effects of RAR CLA on hand joint discomfort.

In sum, RAR-CLA supplementation appears to have a positive influence on improving joint discomfort. However, because there is a relatively long time course for the physiological effects of dietary fatty acids, longer term studies should help investigators better understand the benefits for older adults of RAR-CLA supplementation.

The preceding examples are meant only as illustrations; the following claims define the inventive subject matter.

TABLE 1

Mean (±SD) energy, carbohydrate, protein, and fat intakes across each three-day period at pre- and post-supplementation in men and women.

|  |  | Visit 1: Pre-supplementation | | Visit 2: Post-supplementation | |
|---|---|---|---|---|---|
|  |  | RAR-CLA | PLA | RAR-CLA | PLA |
| Men | Energy (kcal) | 1888.6 (±494.6)[a] | 1824.4 (±327.9)[a] | 1949.4 (±506.0)[a] | 1935.2 (±815.4)[a] |
|  | Carbohydrate (g) | 236.6 (±86.6)[a] | 233.9 (±48.4)[a] | 257.3 (±80.5)[a] | 225.0 (±84.0)[a] |
|  | Protein (g) | 72.9 (±22.4)[a] | 68.2 (±12.3)[a] | 71.4 (±38.0)[a] | 80.9 (±33.0)[a] |
|  | Fat (g) | 65.4 (±22.7) | 68.4 (±26.1) | 67.7 (±32.3) | 77.3 (±45.3) |
| Women | Energy (kcal) | 1601.4 (±253.9) | 1650.9 (±362.2) | 1604.7 (±377.7) | 1627.4 (±317.7) |
|  | Carbohydrate (g) | 192.8 (±49.1) | 203.9 (±70.6) | 176.0 (±29.8) | 203.9 (±54.3) |
|  | Protein (g) | 65.4 (±16.2) | 63.4 (±14.1) | 67.4 (±15.3) | 63.0 (±14.8) |
|  | Fat (g) | 59.8 (±16.0) | 60.0 (±16.3) | 68.8 (±30.3) | 60.1 (±12.3) |

[a]Indicates a significant main effect for gender where intake was greater in men than women.

TABLE 2

The % Decrease in Maximal Voluntary Handgrip Strength from Pre- to Post- Handgrip Fatigue Test and Number of Contractions ($HG_{REP}$) Completed During the Handrgrip Fatigue Test in groups A and B at Visit 1 and Visit 2 in men and women.

|  | Visit 1: Pre-supplementation | | | | Visit 2: Post-supplementation | | | |
|---|---|---|---|---|---|---|---|---|
|  | RAR-CLA | | PLA | | RAR-CLA | | PLA | |
|  | Men | Women | Men | Women | Men | Women | Men | Women |
| % Decrease | 45.9 (±22.5) | 42.8 (±22.7) | 43.0 (±14.8) | 36.4 (±19.1) | 42.9 (±20.6) | 42.5 (±19.4) | 41.0 (±28.4) | 41.7 (±25.9) |
| $HG_{REP}$ | 44.7 (±22.0) | 45.0 (±25.8) | 53.3 (±35.3) | 52.9 (±34.9) | 39.4 (±16.4) | 51.5 (±29.3) | 63.1 (±58.5) | 57.5 (±52.9) |

TABLE 3A and 3B

The mean (±SD) maximal voluntary isometric handgrip contraction (MVIC) strength before (Pre) and after (Post) the handgrip fatigue test and joint discomfort ratings before (Pre), after (Post), and 48 h after (48 h Post) in the RAR CLA and PLA groups at Visits 1 and 2 in men and women.

|  |  | Visit 1: Pre-supplementation | | | | | |
|---|---|---|---|---|---|---|---|
|  |  | Pre | | Post | | 48 h Post | |
|  |  | RAR CLA | PLA | RAR CLA | PLA | RAR CLA | PLA |
| Men | MVIC (kg) | 42.3 (±8.2)[a] | 37.2 (±11.5)[a] | 29.3 (±5.5)[a] | 26.1 (±7.7)[a] | — | — |
|  | Joint Discomfort (mm) | 12.2 (±15.3)[b] | 22.4 (±27.8)[b] | 73.5 (±22.1)[b] | 65.4 (±39.9)[b] | 2.2 (±4.8)[b] | 0.0 (±0.0)[b] |
| Women | MVIC (kg) | 29.8 (±6.2) | 27.1 (±5.0) | 21.5 (±5.9) | 20.2 (±4.4) | — | — |
|  | Joint Discomfort (mm) | 13.6 (±16.0) | 13.9 (±18.1) | 48.5 (±32.1) | 42.5 (±31.5) | 2.1 (±8.9) | 4.0 (±8.1) |

[a]Indicates a significant time × gender interaction. Handgrip MVIC decreased from Pre to Post in both men and women. However, handgrip MVIC was greater in men than women at Pre and Post.

[b]Indicates a significant time × gender interaction. Hand joint discomfort increased from Pre to Post and then decreased from Post to 48 h Post such that joint discomfort was lower at 48 h Post than Pre for both men and women. Joint discomfort was greater in men than women at Post.

TABLES 3A and 3B

The mean (±SD) maximal voluntary isometric handgrip contraction (MVIC) strength before (Pre) and after (Post) the handgrip fatigue test and joint discomfort ratings before (Pre), after (Post), and 48 h after (48 h Post) in the RAR CLA and PLA groups at Visits 1 and 2 in men and women.

|  |  | Visit 2: Post-supplementation | | | | | |
|---|---|---|---|---|---|---|---|
|  |  | Pre | | Post | | 48 h Post | |
|  |  | RAR CLA | PLA | RAR CLA | PLA | RAR CLA | PLA |
| Men | MVIC (kg) | 38.7 (±6.7)$^a$ | 36.2 (±10.2)$^a$ | 27.3 (±4.9)$^a$ | 26.2 (±7.0)$^a$ | — | — |
|  | Joint Discomfort (mm) | 9.3 (±5.0)$^b$ | 20.0 (±27.7)$^b$ | 65.1 (±38.5)$^b$ | 64.1 (±38.3)$^b$ | 2.5 (±7.9)$^b$ | 1.3 (±3.1)$^b$ |
| Women | MVIC (kg) | 29.5 (±5.5) | 27.5 (±6.5) | 21.0 (±4.7) | 20.0 (±5.6) | — | — |
|  | Joint Discomfort (mm) | 15.6 (±21.9) | 12.5 (±19.3) | 42.5 (±32.0) | 49.7 (±37.6) | 4.3 (±15.0) | 1.8 (±3.6) |

$^a$Indicates a significant time × gender interaction. Handgrip MVIC decreased from Pre to Post in both men and women. However, handgrip MVIC was greater in men than women at Pre and Post.
$^b$Indicates a significant time × gender interaction. Hand joint discomfort increased from Pre to Post and then decreased from Post to 48 h Post such that joint discomfort was lower at 48 h Post than Pre for both men and women. Joint discomfort was greater in men than women at Post.

We claim:

1. A method for treating an adult human having or at risk of having impaired joint function, the method comprising administering to the human a dietetic food, medical food, or food supplement comprising a rumenic acid-rich conjugated linoleic acid (RAR-CLA), or a pharmaceutically acceptable salt, ester, metabolic precursor thereof, or mixture thereof, in an amount effective to enhance joint function in the human, wherein the RAR-CLA comprises cis-9, trans-11 linoleic acid and trans-10, cis-12 linoleic acid isomers in a weight ratio of at least 2:1, wherein the metabolic precursor is selected from the group consisting of cis-9, trans-11, cis-13-octadecatrienoic acid, trans-11-octadecenoic acid, cis-9, trans-11-octadecadienol, cis-9, trans-11-octadecadienal, and mixtures thereof.

2. The method of claim 1 wherein the RAR-CLA, salt, ester, metabolic precursor thereof, or mixture thereof is administered in an amount of at least 10 mg/kg human/day for at least 4 weeks.

3. The method of claim 1 wherein the RAR-CLA, salt, ester, metabolic precursor thereof, or mixture thereof is administered in an amount within the range of 50 to 200 mg/kg human/day for at least 8 weeks.

4. The method of claim 1 wherein the human has reached at least 50% of life expectancy.

5. The method of claim 1 wherein the human has reached at least 70% of life expectancy.

6. The method of claim 1 wherein the dietetic food, medical food, or food supplement has a lipid content and a CLA-containing portion of the lipid content, and at least 10 wt. % of the CLA-containing portion of the lipid content of the dietetic food, medical food, or food supplement comprises the RAR-CLA, salt, ester, metabolic precursor thereof, or mixture thereof.

7. The method of claim 1 wherein the dietetic food, medical food, or food supplement has a lipid content and a CLA-containing portion of the lipid content, and at least 35 wt. % of the CLA-containing portion of the lipid content of the dietetic food, medical food, or food supplement comprises the RAR-CLA, salt, ester, metabolic precursor thereof, or mixture thereof.

8. The method of claim 1 wherein the RAR-CLA comprises cis-9, trans-11 linoleic acid and trans-10, cis-12 linoleic acid isomers in a weight ratio of at least 3:1.

9. The method of claim 1 wherein the RAR-CLA comprises cis-9, trans-11 linoleic acid and trans-10, cis-12 linoleic acid isomers in a weight ratio of at least 3.5:1.

10. A method of treating an adult human having joint discomfort, the method comprising administering to the human a dietetic food, medical food, or food supplement comprising a rumenic acid-rich conjugated linoleic acid (RAR-CLA), or a pharmaceutically acceptable salt, ester, metabolic precursor thereof, or mixture thereof, in an amount effective to alleviate joint discomfort in the human, wherein the RAR-CLA comprises cis-9, trans-11 linoleic acid and trans-10, cis-12 linoleic acid isomers in a weight ratio of at least 2:1, and wherein the metabolic precursor is selected from the group consisting of cis-9, trans-11, cis-13-octadecatrienoic acid, trans-11-octadecenoic acid, cis-9, trans-11-octadecadienol, cis-9, trans-11-octadecadienal, and mixtures thereof.

11. The method of claim 10 wherein the RAR-CLA, salt, ester, metabolic precursor thereof, or mixture thereof is administered in an amount of at least 10 mg/kg human/day for at least 4 weeks.

12. The method of claim 10 wherein the RAR-CLA, salt, ester, metabolic precursor thereof, or mixture thereof is administered in an amount within the range of 50 to 200 mg/kg human/day for at least 8 weeks.

13. The method of claim 10 wherein the human has reached at least 50% of life expectancy.

14. The method of claim 10 wherein the human has reached at least 70% of life expectancy.

15. The method of claim 10 wherein the dietetic food, medical food, or food supplement has a lipid content and a CLA-containing portion of the lipid content, and at least 10 wt. % of the CLA-containing portion of the lipid content of the dietetic food, medical food, or food supplement comprises the RAR-CLA, salt, ester, metabolic precursor thereof, or mixture thereof.

16. The method of claim 10 wherein the dietetic food, medical food, or food supplement has a lipid content and a CLA-containing portion of the lipid content, and at least 35 wt. % of the CLA-containing portion of the lipid content of the dietetic food, medical food, or food supplement comprises the RAR-CLA, salt, ester, metabolic precursor thereof, or mixture thereof.

17. The method of claim 10 wherein the RAR-CLA comprises cis-9, trans-11 linoleic acid and trans-10, cis-12 linoleic acid isomers in a weight ratio of at least 3:1.

18. The method of claim 10 wherein the RAR-CLA comprises cis-9, trans-11 linoleic acid and trans-10, cis-12 linoleic acid isomers in a weight ratio of at least 3.5:1.

\* \* \* \* \*